Figure 1:
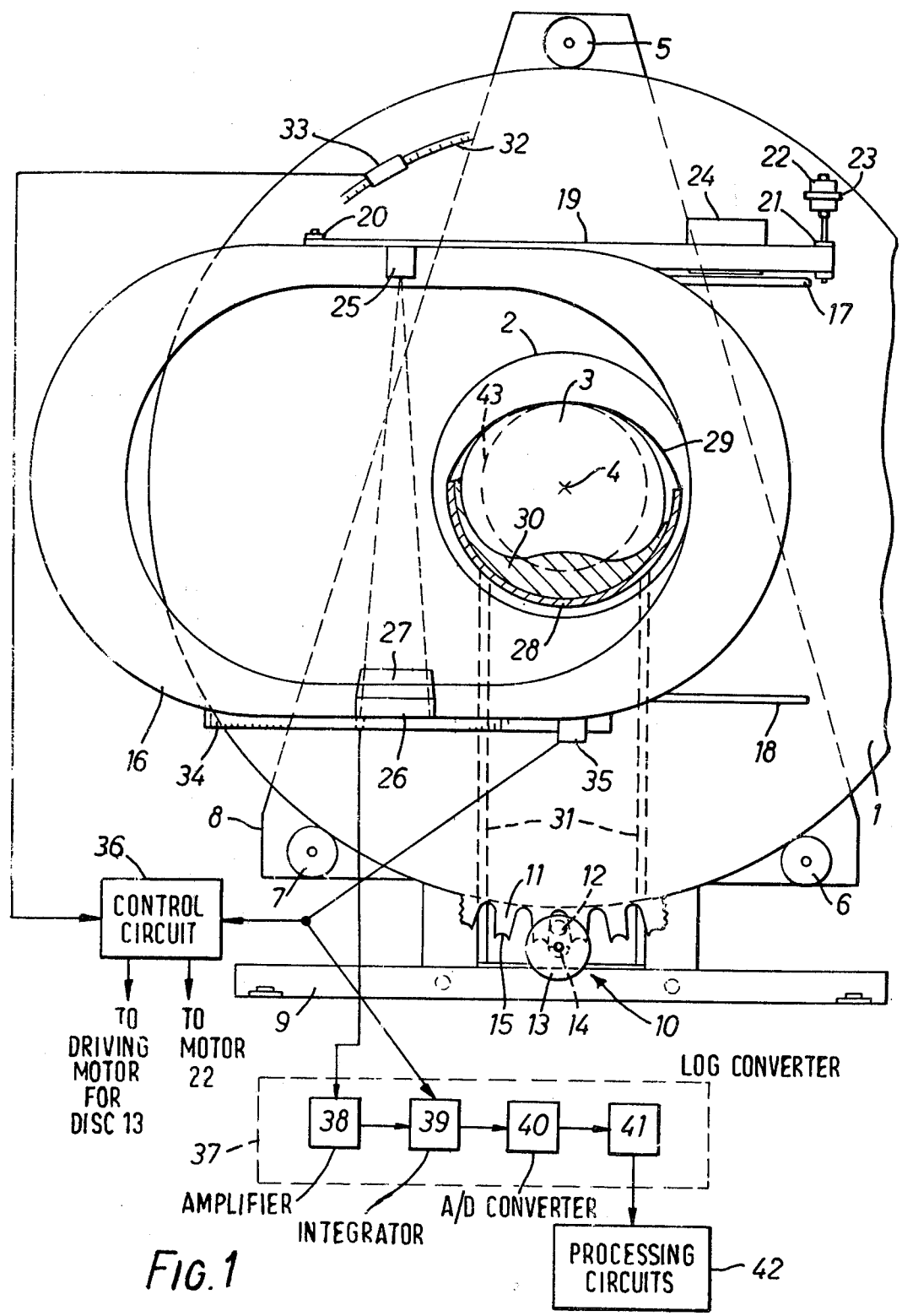

United States Patent [19]

Bates

[11] 4,117,336

[45] Sep. 26, 1978

[54] COMPUTERIZED RADIOGRAPHY WITH MEANS TO PROCESS ONLY SELECTED SIGNALS

[75] Inventor: Stephen Ronald Bates, Bourne End, England

[73] Assignee: EMI Limited, Hayes, England

[21] Appl. No.: 785,186

[22] Filed: Apr. 6, 1977

[30] Foreign Application Priority Data

Apr. 15, 1976 [GB] United Kingdom ............... 15515/76

[51] Int. Cl.² .............................................. A61B 6/02
[52] U.S. Cl. ............................ 250/445 T; 250/363 S
[58] Field of Search .................... 250/44 ST, 360, 366, 250/369, 363 S

[56] References Cited

U.S. PATENT DOCUMENTS

| 3,924,129 | 12/1975 | LeMay | 250/445 T |
| 3,946,234 | 3/1976 | Hounsfield | 250/445 T |

*Primary Examiner*—Alfred E. Smith
*Assistant Examiner*—T. N. Grigsby
*Attorney, Agent, or Firm*—Cooper, Dunham, Clark, Griffin & Moran

[57] ABSTRACT

In order to obtain rapidly a representation of the results of a computerized tomographic examination of a patient, some of the data obtained during the examination is ignored. The representation is thus produced rapidly, as desired, but on the basis of less information than is actually available. A representation using all the available information can be produced later, as required.

9 Claims, 2 Drawing Figures

COMPUTERIZED RADIOGRAPHY WITH MEANS TO PROCESS ONLY SELECTED SIGNALS

The present invention relates to radiography, and it relates especially, though not exclusively, to radiographic apparatus by means of which it is possible to determine the absorption or transmission coefficients at a plurality of locations distributed over a planar slice cross-sectionally disposed in a body under examination. An apparatus for, and method of, effecting the evaluation referred to above is described and claimed in U.S. Pat. No. 3,778,614.

The technique for such evaluation involves determining the amount of radiation absorbed on traversing each of a large number of linear paths through the body in the plane of the slice and suitably processing the absorption values so determined. In order to project the radiation through the body along all of the aforementioned paths, the source of the radiation and an associated detector means are scanned relative to the body.

The aforementioned Patent Specification discloses techniques for effecting the scanning and the processing; a faster scanning technique being described and claimed in U.S. Pat. No. 3,946,234, whereas a faster processing technique is described and claimed in U.S. Pat. No. 3,924,129.

The processing technique disclosed in the aforementioned U.S. Pat. No. 3,924,129 involves a form of convolution of the determined absorption data in which the data are assembled in sets corresponding to parallel paths through the body and each determined absorption value is modified by being combined with the values relating to other paths of the same set, each weighted in accordance with a weighting function which decreases in amplitude with increasing distance of the path corresponding to the value being weighted from the path corresponding to the value being modified. The modified values are then superimposed in layergram format. This technique is known as a compensated layergram operation.

Whilst the patient is disposed in the examining apparatus, it is expedient to examine several adjacent and substantially parallel slices of his body. A difficulty arises, however, in that the data can be acquired by means of the scanning technique described and claimed in the aforementioned U.S. Pat. No. 3,946,234 at a rate which substantially exceeds the rate of processing even when the processing is carried out in the manner described and claimed in the aforementioned U.S. Pat. No. 3,924,129. This means that, if no steps were taken to the contrary, the data could be acquired for several slices before the representation relating to the first slice examined were produced. Thus if the apparatus is not operating correctly, the operator of the apparatus will have no knowledge of this until the first representation is produced, and in the meantime the patient has possibly been subjected to radiation to no good purpose. Since, if the apparatus has not been functioning correctly, all of the slices examined up to the time of discovery of the incorrect functioning (i.e., the time of display of the first representation) will have to be re-examined, this time lag in discovery of incorrect functioning of the apparatus is undesirable from the point of view of patient throughput as well as the aforementioned unnecessary irradiation of the patient.

It is an object of this invention to reduce the aforementioned difficulty by providing the representation of the first slice, at least, with a reduced delay compared with that which has occurred hitherto.

According to the invention there is provided radiographic apparatus including means for projecting radiation through a body along a plurality of coplanar sets of paths, each set including paths distributed across a substantial region of said body in said plane, and the paths of each set being orientated at a respective angle, or mean angle, in the plane, detector means for detecting the radiation emergent from the body along each path and processing means for processing output signals derived from said detector means and indicative of the absorption suffered by the radiation on traversing the paths of some only of said sets to evaluate the absorption coefficient, with respect to said radiation, at each of a plurality of locations distributed over a predetermined region in the plane. Preferably switchable means is provided such that said processing means can be controlled so as to optionally utilise output signals indicative of the absorption suffered by the radiation on traversing the paths of all of said sets. Preferably also, of the sets of paths giving rise to the output signals operated on by said processing means, each set is separated in angle from its neighbours by a small angle, for example one degree or less.

Figure 2:
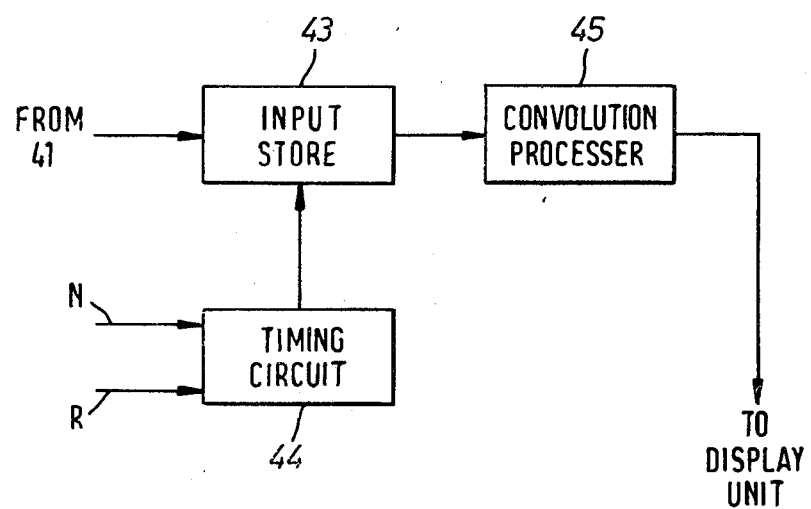

In order that the invention may be clearly understood and readily carried into effect, one embodiment thereof will now be described, by way of example only, with reference to the accompanying drawings of which:

FIG. 1 shows, in front elevational view, radiographic apparatus in conjunction with which the invention may be used with advantage, and FIG. 2 shows, in block schematic form, part of an apparatus in accordance with one example of the invention.

Referring now to FIG. 1, the apparatus shown therein is similar in principle to the apparatus described in the aforementioned U.S. Pat. No. 3,946,234. A turntable member 1 having a central aperture 2, to accommodate a body 3 to be examined, is mounted vertically for rotation about an axis 4 which is disposed centrally in the aperture 2. The member 1 is upported on three rotatable bearings 5, 6 and 7 which are journalled in a main frame 8 for the apparatus. The frame 8 remains stationary, being rigidly secured to a pedestal 9, and can take any suitable form, although it must of course be formed with an aperture coincident with the aperture 2.

The member 1 can be rotated in angular steps of (in this example) ten degrees by means of a Geneva mechanism generally shown at 10. The periphery of member 1 is formed with suitable prongs such as 11 which define slots arranged to co-operate with a peg 12 on a continuously rotated disc 13 to effect the required step-wise rotary movement. The disc 13 also carries a locking cam 14 which co-operates with suitably shaped recesses such as 15 on the prongs such as 11 to effectively lock the member 1 in its angular position so long as the peg 12 is not in one of the slots formed between adjacent prongs 11. Disc 13 is journalled in the main frame 8 and is driven by an electric motor which is not shown.

Mounted upon the turntable 1, and capable of performing a reciprocating lateral scanning motion relative thereto, is a lightweight but rigid scanning yoke 16. Yoke 16 can move on linear runners 17 and 18 which are fixedly mounted on the rotatable member 1 and are disposed chordally thereof. The lateral scanning motion is imparted to the yoke 16 by virtue of a toothed belt 19, which is stretched between a pair of toothed rollers 20 and 21 journalled in respective brackets (not shown) secured to the member 1, and to which belt the yoke 16 is attached by means of a bracket (not shown). The roller 20 is merely an idler roller, but roller 21 is driven by a reciprocating motor 22 which is attached by a strap-like bracket 23 to the member 1.

A counter-balance weight 24 is secured to the opposite run of belt 19 to the yoke 16 and thus moves in opposition thereto to compensate for out-of-balance forces which would otherwise be set up by the lateral scanning motion of the yoke 16 and its attachments, which will now be described.

Attached to the yoke 16 is a source 25 of penetrating radiation, in this example X-radiation. The radiation is collimated to form a planar, fan-shaped beam, emanating from an effective point source. On the opposite side of yoke 16, with respect to the aperture 2, to the source 25 is an array 26 of thirty detectors sensitive to the radiation generated by the source 25, each viewing the source through a respective collimator; the collimators being disposed in a bank 27. In this example, neighbouring collimators are inclined to each other at an angle of $\frac{1}{3}°$ and since there are thirty detectors, this means that the angular spread of the beam of X-rays generated by the source 25 is about 10°.

The body 3 is supported on a semi-cylindrical, one part bed 28 and is secured thereon by means of straps such as 29. Gaps between the body and the bed are filled with a suitable packing material 30 which preferably absorbs the x-radiation to substantially the same extent as does human tissue. The material 30 is preferably contained in one or more plastic bags. The bed 28 is supported by legs 31 which stand on the pedestal 9.

It will be evident that the stepped, rotational scanning motion imparted by the Geneva mechanism 10 to the member 1 needs to be synchronised with the lateral scanning motion imparted to the yoke 16 by the reciprocating motor 22 and to this end the member 1 is formed with an annular graticule, part of which is shown at 32, and a fixed photodetector 33 is provided, together with a suitable light source (not shown) to provide timing pulses indicative of the passage of markings on the graticule 32 past the photodetector 33. Thus the rotational scanning motion of member 1 can be monitored, and similarly a linear graticule 34 is fixedly attached to the yoke 16 and co-operates with a second photodetector 35, which is mounted on the member 1 so as to rotate therewith, and a similarly mounted light source (not shown) to produce timing pulses indicative of the progress of the lateral scanning. Both graticules 32 and 34 comprise translucent or transparent members bearing opaque lines printed, etched or otherwise provided thereon. The two sets of timing pulses are fed to a control circuit 36 which controls the motor 22 and the motor (not shown) which drives the disc 13 of the Geneva mechanism 10 in such a way that after each step of rotational motion a single lateral scan is carried out to scan the source 25 and the detector array 26 in one direction or the other across the aperture 2. Thus a single lateral scan is carried out for each dwell angle of the member 1, these dwell angles being ten degrees apart.

Each detector in the array 26 comprises, for example, a scintillator crystal (e.g. caesium iodide) and an associated photomultiplier tube, or a photodiode, and thus provides electrical signals indicative of the amount of radiation detected thereby. The electrical signals so provided are applied to respective preprocessing circuits 37, each of which contains an amplifier 38, a resettable integrator 39, an analogue-to-digital converter circuit 40 and a logarithmic converter circuit 41. The integrators 39 are read and reset synchronously and periodically by means of timing pulses derived from the photodetector 35; the arrangement being such that the reading and re-setting occurs some on hundred and sixty times during each lateral scan in either direction. Thus, during a single lateral scan, output signals are provided which are indicative of the absorption suffered by the X-radiation on traversing a set of one hundred and sixty parallel path from the source to the detector at each of thirty angular orientations with respect to the body 3. The member 1 is then rotated through ten degrees and a second group of thirty sets of one hundred and sixty output signals are derived. The process is repeated until the member 1 has been rotated through at least 170°. All of the output signals obtained during the scanning are applied to an input store of a processing circuit 42. The output signals are withdrawn from the store in a suitable sequence and used to evaluate the absorption coefficient, with respect to the radiation used, at a plurality of locations distributed over the slice of the body 3 which lies in the plane of the beam of X-rays generated by the source 25.

Preferably the processing is carried out in accordance with the technique described and claimed in U.S. Pat. No. 3,924,129. As previously mentioned, this technique involves a form of convolution and the output signals are processed in sets relating to parallel paths through the body. Each output signal is modified by combining it with weighted components of other output signals of its own set; the weighting being in accordance with a function which is negative, and decreases in amplitude as the distance from the path giving rise to the output signal being weighted to the path giving rise to the output signal being modified increases. The modified output signals are then additively combined in accordance with the inter relationship of the paths to which they relate in accordance with a layergramming procedure, the modification of the output signals being such as to compensate for the known inaccuracies of conventional layergrams.

In order to fulfill the aforementioned object of this invention, and thereby provide, with reduced delay, a representation of (at least) the first slice of the body examined, this example of the invention includes means for selecting from the stored output signals only those relating to every third set of paths through the body. These selected output signals are then processed in the aforementioned manner, but since the processing circuits have substantially fewer (66⅔% fewer in this example) output signals to deal with, the representation is produced rapidly. The resolution at the periphery of the slice of the body is somewhat degraded as compared with the resolution achievable by processing all of the output signals, but that at the centre of the slice is sufficiently high to permit an operator to ascertain whether or not the apparatus is operating correctly. By means of this technique it is feasible to await the production of this first representation before examining any other slices of the body. Alternatively, if it is not desired to wait, then the examination of other slices may be allowed to proceed although it will be appreciated that, because of the rapid production of the first representation, the examination of other slices will not have proceeded so far as it would have, in the absence of the invention, before the representation is produced. Thus the aforementioned difficulties of unnecessary irradiation of the patient and reduction in patient throughput, should re-examination prove necessary, are both reduced.

Referring now to FIG. 2, which shows some of the components od the processing circuits 42 in FIG. 1, the signals from the log converter 41 are applied, in order of receipt, to an input store 43 under the influence of a timing circuit 44.

In accordance with a command signal applied to the circuit 44 over a conductor N or a conductor R, the processing adopts a normal or rapid operating condition respectively. In the normal condition, all sets of output signals contained in store 43 are applied in sequence to a convolution processing unit 45 and the usual high resolution representation is produced. If the rapid operation is required, however, a command signal sent over the conductor R to the circuit 44 causes only these output signals relating to every third set of paths to be applied to the unit 45. For example, if the detectors in the array 26 are numbered D1 to D30, then in this example only those output signals derived from detectors D1, D4, D7, D10 . . . D28 would be used. Since neighbouring detectors provide output signals relating to paths disposed at $\frac{1}{3}°$ to one another, the signals actually used in the "rapid" operating condition relate to sets of paths of which neighbouring sets are disposed at about 1° to one another.

Of course, other arrangements could be used. For example every fourth set of output signals could be used if desired.

In this example, only the output signals relating to the first examined slice are processed in the rapid mode to ensure that the apparatus is operating correctly. Thereafter, a command signal is sent to the circuit 44 over the conductor N to cause the processing circuits to operate in their normal mode. The first operation carried out after reverting to the normal mode is to use the remaining output signals stored in the store 43 to improve the resolution of the representation of the first slice examined. Subsequent slices are processed with full resolution.

It is possible, instead of using one processing unit such as 45 to operate in both the rapid and normal modes, to provide two separate processing units, one for each mode, and to ensure that the unit for rapid mode operations only receives one third of the output signals provided by the detectors whilst the unit for normal mode operation receives all of the said output signals. This would enable all representations of slices examined to be produced rapidly. The two processing units need not be identical; it may be advantageous to construct the unit for rapid mode operation in a more rudimentary form than the other unit and to omit, for example, interpolating circuits which would be used in the normal mode unit for ensuring that the evaluated coefficients are accurately attributed to the centres of the elements in the body to which they relate.

Additional refinements may be made to the apparatus shown in FIG. 1 without departing from the scope of the invention. For example blocks of X-ray absorbent material could be disposed between the source 25 and the body 3 and possibly also between the body 3 and the detector array 26 to tend to reduce variations in the degree of absorption suffered by the radiation on traversing paths of different lengths through the body 3. Moreover, the blocks may be arranged to impart a specified attenuation to the radiation when it traverses paths wholly outside the body 3 and its supporting bed so as to permit the sensitivities of the various detectors to be monitored.

In some circumstances, it can be difficult to physically accommodate the thirty detectors in side-by-side relationship in the array 26 and in such cases it is desrable to stagger the detectors in distance from the source the stagger, of course, being kept to a minimum.

Finally, it will of course be evident that the pedestal 9, or another pedestal to which it is secured, have to be sufficiently high to ensure ground clearance of the yoke 16.

What I claim is:

1. Radiographic apparatus including means for projecting radiation through a body along a plurality of coplanar sets of paths, each set including paths distributed across a substantial region of said body in said plane, and the paths of each set being orientated at a respective angle, or mean angle, in the plane, detector means for detecting the radiation emergent from the body along each path and processing means for processing output signals derived from said detector means and indicative of the absorption suffered by the radiation on traversing the paths of some only of said sets to evaluate the absorption coefficient, with respect to said radiation, at each of a plurality of locations distributed over a predetermined region in the plane.

2. Apparatus according to claim 1 including switchable means for causing said processing means to process either the output signals relating to said some only of said sets or the output signals relating to substantially all of said sets.

3. Apparatus according to claim 1 including means for selecting said some only of said sets such that each set is separated in angle from neighbouring sets by about one degree.

4. Apparatus according to claim 1 wherein each set of paths comprises a plurality of paths substantially parallel to each other.

5. Apparatus according to claim 1 wherein said some only of said paths constitute about one third of the total number of said paths.

6. Apparatus according to claim 1 wherein said means for projecting said radiation through said body includes a source of a fan-shaped distribution of said radiation and means for scanning said source around said body in a series of alternate lateral traverses and rotational steps.

7. Apparatus according to claim 6 wherein said detector means comprises an array of detector devices extending across said distribution of radiation and constrained to scan around said body concomitantly with the scanning of said source.

8. A medical radiographic apparatus for examining a patient by X-radiation comprising:
means for projecting X-radiation along a plurality of substantially coplanar paths from different locations distributed in an orbit around the patient, all of said paths being substantially within a slice of the patient;
means for detecting the X-radiation which has traversed the patient along each of said paths and for forming output signals corresponding to the radiation detected along said paths;
means for selecting only output signals which correspond to paths spaced from each other by other paths; and
circuit means for processing only the output signals selected by the selecting means in accordance with a compensated layergram technique to derive a map of the distribution of X-radiation absorption in the slice, said map being based only on said selected output signals.

9. A medical radiographic apparatus as in claim 8 including means for storing the output signals in sets corresponding to sets of paths of which all the paths of one set are parallel to each other and the paths of the different sets are at an angle to each other, and where the selecting means include means for selecting only sets of output signals for sets of paths which are angularly spaced from each other by sets of paths for non-selected output signals.

* * * * *